US005291925A

United States Patent [19]

[11] Patent Number: 5,291,925

[45] Date of Patent: Mar. 8, 1994

Marrucchi

[54] EQUIPMENT FOR FORMING TEMPORARY CONNECTIONS FOR THE TRANSFER OF OBJECTS BETWEEN DISCONTINUOUS CONFINED VOLUMES

[76] Inventor: Piero Marrucchi, Piazza Pitti No. 17, 50125 Firenze, Italy

[21] Appl. No.: 944,897

[22] Filed: Sep. 15, 1992

[30] Foreign Application Priority Data

Sep. 18, 1991 [IT] Italy .......... FI/91/A 230

[51] Int. Cl.[5] .......... B65B 25/08; A61M 5/00

[52] U.S. Cl. .......... 141/329; 141/98; 141/319; 141/312; 414/217; 414/222; 53/468

[58] Field of Search .......... 414/217, 222; 141/1, 141/98, 329, 330, 319, 312; 53/568; 206/219

[56] References Cited

U.S. PATENT DOCUMENTS

| | | | |
|---|---|---|---|
| 4,534,389 | 8/1985 | Tullis | 141/98 |
| 4,724,874 | 2/1988 | Parikh et al. | 141/98 |
| 4,732,527 | 3/1988 | Conche | 414/217 X |
| 4,793,475 | 12/1988 | Itzel | 206/219 X |
| 4,821,875 | 4/1989 | Groves et al. | 206/219 |
| 5,117,875 | 6/1992 | Marrucchi | 141/1 |
| 5,152,965 | 10/1992 | Fisk et al. | 206/219 X |

*Primary Examiner*—Ernest G. Cusick
*Attorney, Agent, or Firm*—McGlew & Tuttle

[57] ABSTRACT

An isolating chamber (1) with an annular connector (5) defines an access opening with one dimension greater than that perpendicular thereto and with an internal wall (5A) of constant section to allow the hermetic sliding of successive closure pieces (7,7X) which have a closure membrane (14,14X), and an annular cutting device (9B) for the membrane and for another membrane joined thereto. Each transfer machine (3) has a passageways slot and a closure membrane (22). The two membranes are designed to adhere to each other during the joining up of the two confined volumes (1,3) and are cut by the annular cutting device (9B) to define a discoid (D) with two at least peripherally joined thicknesses. The discoid can be removed into one of the confined volumes to provide the passage between the two the confined volumes; a subsequent uncut closure piece (7X) can be installed in the connector (5) from the interior of the isolating chamber (1), in order to replace the previous closure piece (7) which thus can be removed.

9 Claims, 6 Drawing Sheets

Fig. 2
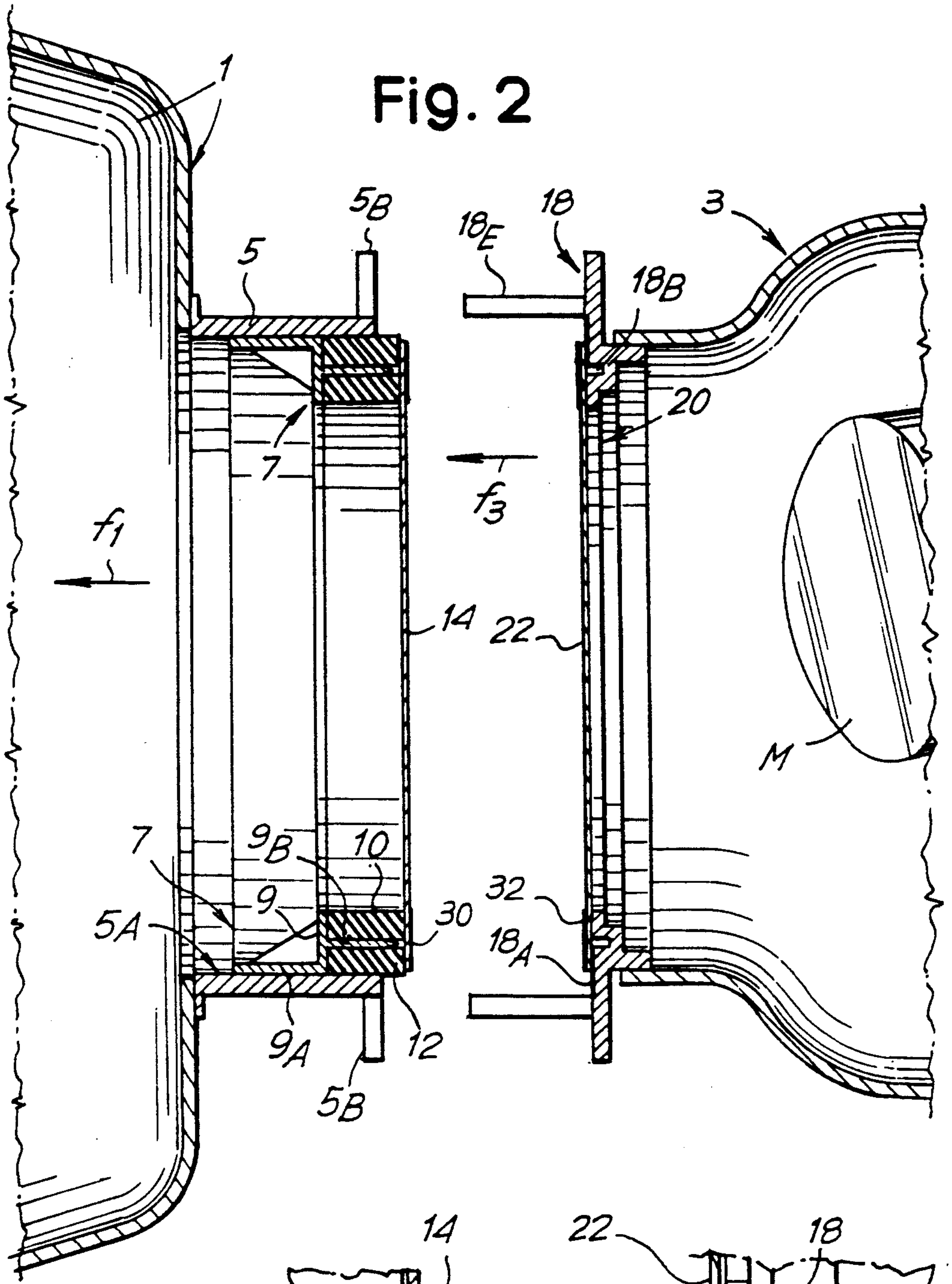
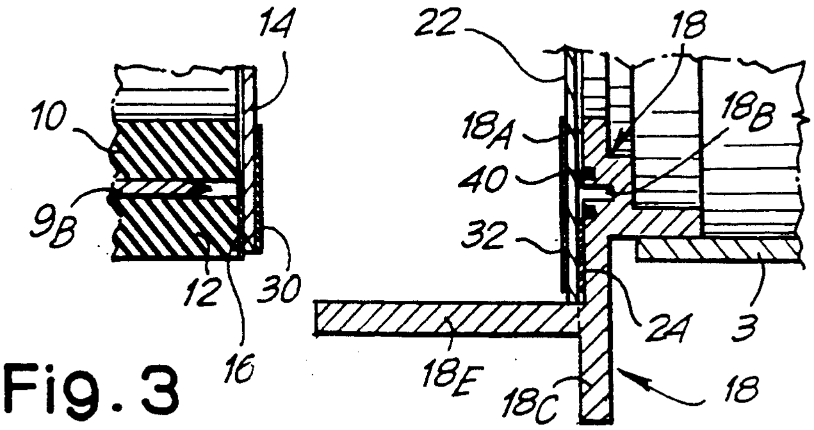
Fig. 3

EQUIPMENT FOR FORMING TEMPORARY CONNECTIONS FOR THE TRANSFER OF OBJECTS BETWEEN DISCONTINUOUS CONFINED VOLUMES

FIELD AND BACKGROUND OF THE INVENTION

The invention relates to improved equipment for forming repeated connections between discontinuous confined volumes, particularly between an isolating chamber and one or more transfer machines, with formation of slots and in conditions of sterility or isolation or conditioning, using pieces which may be single-use pieces. These and other objects and advantages will be clear from the following text.

SUMMARY AND OBJECTS OF THE INVENTION

Basically, the equipment of the invention comprises on the isolating chamber an annular connector defining an access opening, with one dimension greater than that perpendicular thereto and with an internal wall of constant section to allow the hermetic sliding of successive closure pieces which each have a closure membrane and an annular cutting means for said membrane and for another membrane joined thereto. In the transfer machine, or in each transfer machine, there are provided a frame defining a passageway slot and a closure membrane fastened to said frame. Said two membranes are designed to adhere to each other during the joining up of the two confined volumes and said membranes, immediately after being joined, are cut by said annular cutting means to define a discoid with two at least peripherally joined thicknesses, which can be removed into one of the confined volumes to provide the passage between the two said confined volumes; a subsequent uncut closure piece, contained in one of said two confined volumes, can be installed in said connector from the interior of said isolating chamber, to replace the previous closure piece which thus can be removed.

Other characteristics are illustrated in the text and drawings, and are claimed.

In particular each subsequent closure piece may be advantageously fitted with a cap, which covers the membrane on the surface facing out away from the isolating chamber, in whose connector said subsequent closure piece may be installed; said cap is designed to be detached from said subsequent closure piece and joined to the closure piece, which is removed with the transfer machine; the internal volume of the transfer machine is thus once again isolated from the external environment.

The equipment may comprise heating means which cooperate with said annular cutting means to form along the cutting line a seal between the two cut thicknesses of the membranes along the periphery of the discoid of two peripherally joined thicknesses, and along the internal periphery of the annular remnant.

Means may be provided for forming the external mechanical connection, when required, between said connector of the isolating chamber and the frame of the transfer machine, which are to be placed temporarily in communication with each other.

Removable covers, such as films, may be provided to protect the adhesive annular rings of the external surfaces of the two membranes that are to be joined, and will be removed at the moment of the joining up of the two confined volumes.

The embodiment of the equipment is such as to allow the production of single-use components or more generally components that are very simple and cheap and that provide high performance.

BRIEF DESCRIPTION OF THE DRAWING

The invention will be understood more clearly from an examination of the description and of the attached drawing, which latter shows a practical and nonrestrictive embodiment of said invention. In the drawing:

FIG. 2 shows the two confined volumes in longitudinal section and ready to be joined together;

FIG. 3 shows an enlarged detail of FIG. 2;

DETAILED DESCRIPTION OF THE PREFERRED EMBODIMENT

Figure 1:
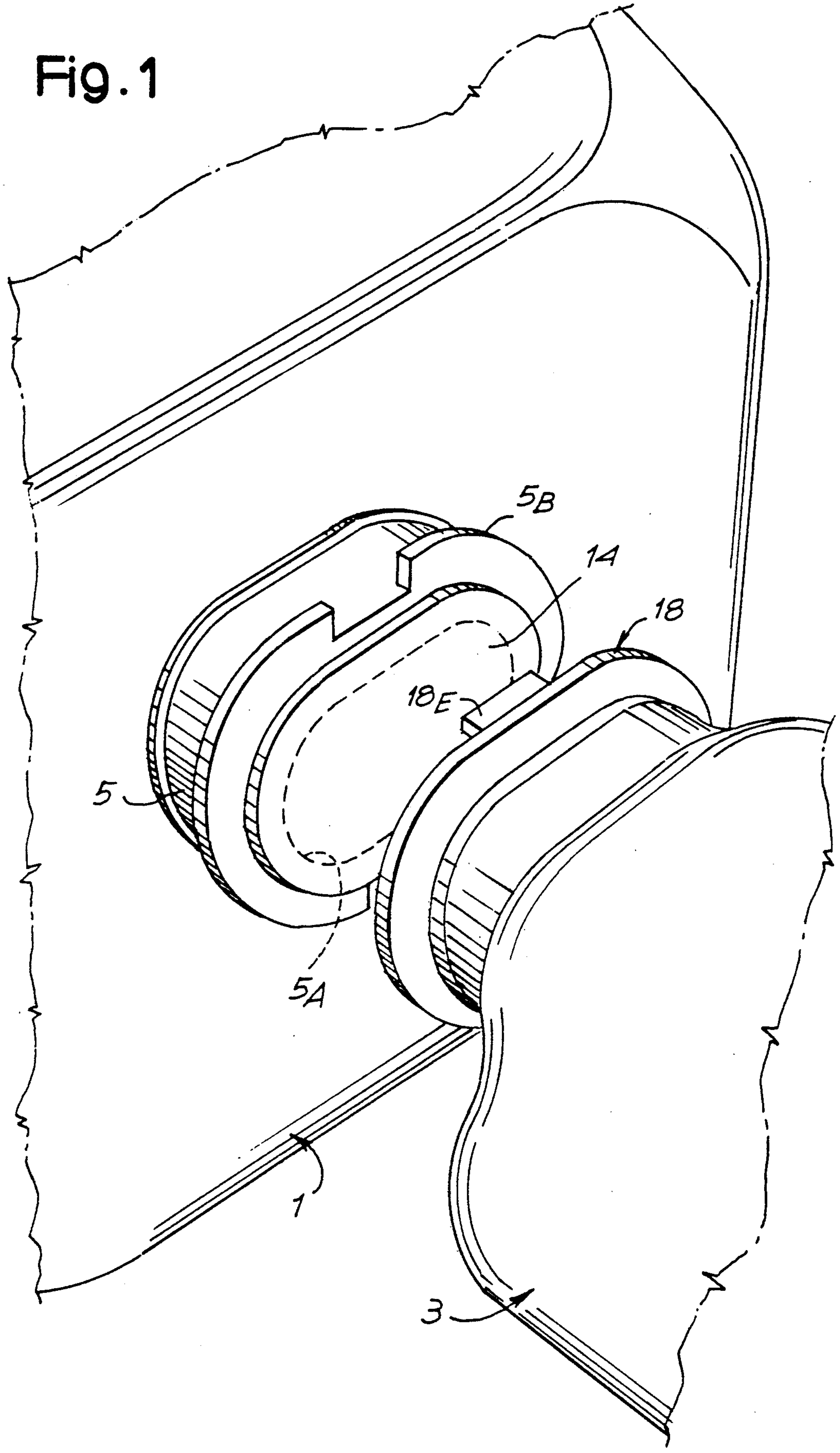
FIG. 1 shows a partial perspective view of two confined volumes presented for joining up.

As the attached drawing shows, 1 indicates one of the two confined volumes and in particular what is referred to as an isolating chamber which is that in which a process or operation is carried out and to which certain accessories must be supplied through one or more successive confined volumes, referred to as transfer machines, one of which is indicated by 3. They may be of the throw-away sort or only partly recyclable. Between the two confined volumes, a communication must be established that is totally isolated from the external environment and that will allow the transfer or objects or components between one of the confined volumes and the other and hence the formation of a passage, that is of a comparatively large opening, the whole with operations that must be as fast as possible and with equipment that is very low-cost and simple.

In the confined volume 1 forming the isolating chamber is a connector 5 with an internal wall 5A which defines the passage to be established between the two confined volumes. This wall 5A has two central perpendicular dimensions which are different from each other so that a support having a slot corresponding to the opening defined by the wall 5A can be inserted through the opening defined by said wall 5A and hence by said connector by arranging it at an angle so that it moves with its minor dimension in line with the major dimension of the opening defined by said wall 5A. The wall 5A is a prismatic or cylindrical wall having the abovementioned shape and externally the connector 5 has flange means 5B with elements to enable it to be joined to another confined volume such as 3.

Inside the connector 5, that is inside the wall 5A, there may slidingly and sealingly be received a closure piece indicated as a whole by 7, which comprises in particular a rigid annular structure 9 with a part 9A which slides along the wall 5 being adjacent to the latter and being capable of being engaged with it so as not to slide towards the interior of the container 1, that is in the direction of the arrow fl in FIG. 2. The annular structure 9 has a cylindrical wall 9B shaped with a terminal cutting edge facing out from the confined volume 1, this part 9B forming an annular cutting means. This annular cutting means 9B is flanked on the inside by a comparatively soft bushing 10 and on the outside by another, likewise soft bushing 12 that is able to adhere to the wall 5A, so providing a hermetic seal between the inside and the outside, and that can also allow the sliding of the piece 7 along the wall 5A of the connector 5, especially from the inside toward the outside. In the position shown in FIG. 2, the piece 7 is engaged with the means which prevent it from moving in the direction of the arrow fl and which can be represented by serrations on the wall 9A which engage in suitable saw-tooth indentations formed in the wall 5A; said piece 7 projects slightly with its elastic bushings 10 and 12 beyond the terminal flange 5B of the connector 5. A first membrane 14 for closing the isolating chamber 1 is laid against the outward frontal surfaces of the bushings 10 and 12; said membrane 14 is bonded by a cement around its perimeter as indicated at 16 to the outward frontal surface of the outer bushing 12. The membrane 14 can be cut by the cutting edge of the annular cutting means represented by the part 9B of the abovementioned annular structure 9, when the bushings 10 and 12 are frontally compressed sufficiently to cause the cutting edge of the cylindrical wall 9B to project.

The confined volume 3—which represents what is referred to as a transfer machine intended to be joined up temporarily with the confined volume 1 to permit communication between these two confined volumes—comprises a frame 18 which defines a passageway slot 20 closed by a membrane 22 which closes off the transfer machine and is similar in shape to the membrane 14. This membrane 22 is supported against the outward frontal surface 18A of the frame 18; the surface 18A is interrupted by an annular groove 18B which corresponds to the annular cutting means 9B so as to cooperate with the latter in the manner indicated below. The frame 18 has a projecting flange part 18C equipped with mechanical joining means (not shown) designed to cooperate with the corresponding means which are provided on the flange 5B of the connector 5. The frame 18 has projecting parts 18E for guiding said frame and hence the transfer machine 3 onto the outside of the connector 5 of the confined volume 1, in such a way as to form a guide for the mechanical joining up of the two confined volumes. By means of an adhesive 24, the membrane 22 adheres around its perimeter to the surface 18A on the outside of the annular groove 18B, and hence opposite the outer bushing 12 of the closure piece 7 which is received in the connector 5, when the two confined volumes are joined up.

Figure 6:
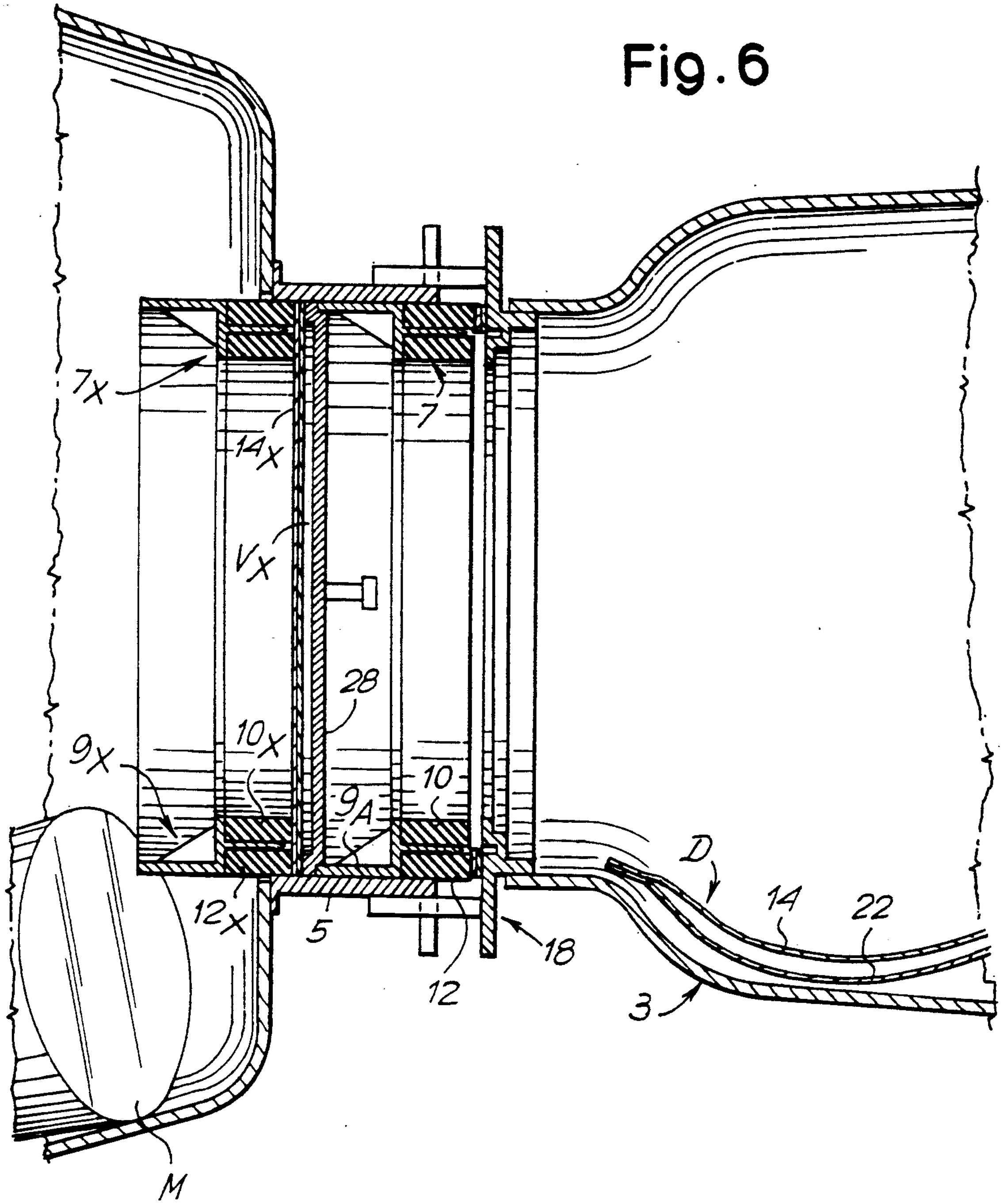
FIG. 6 is similar to FIG. 5 but shows the situation before the removal of the confined volume referred to as the transfer machine.
Figure 7:
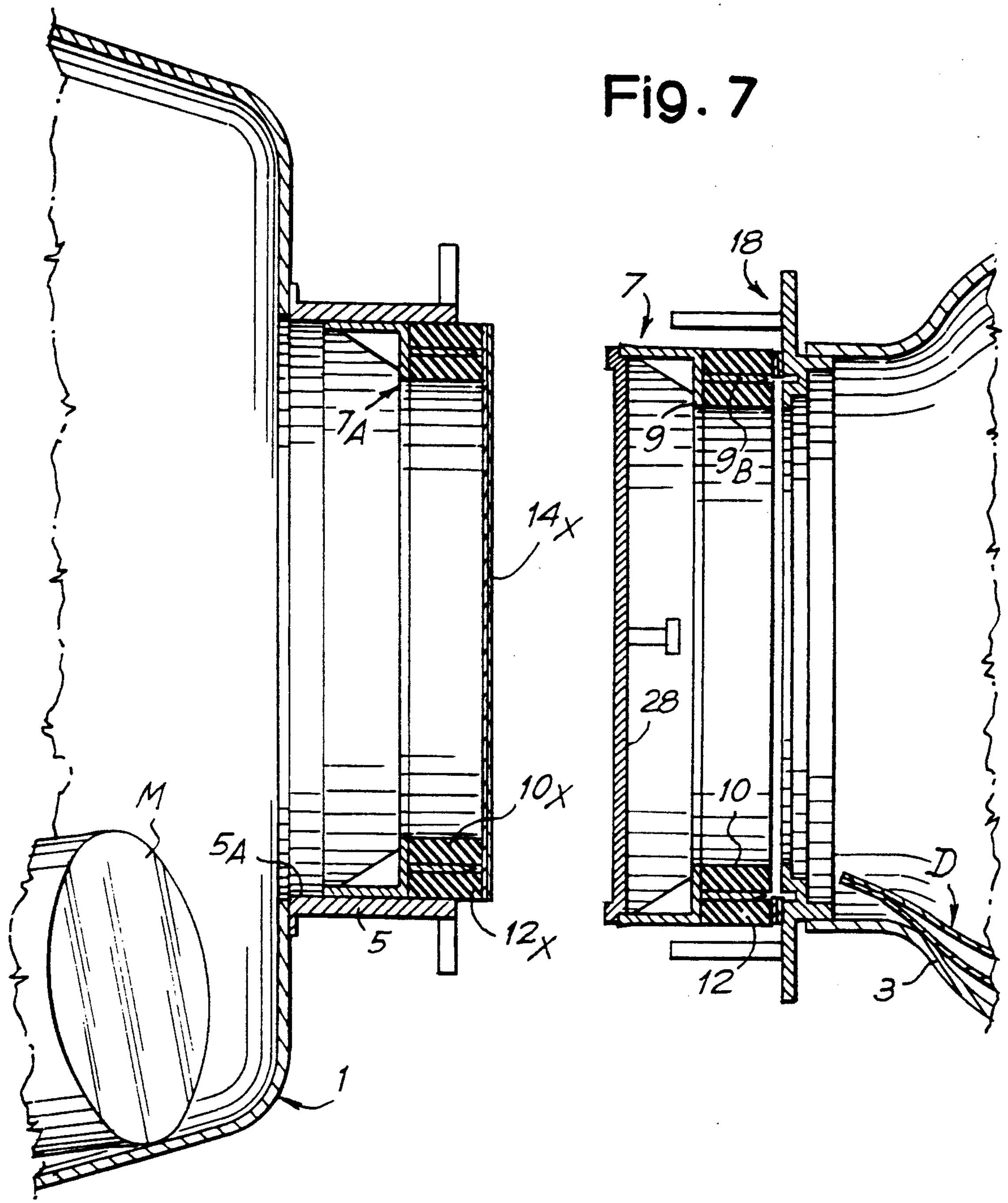
FIG. 7 is similar to FIG. 6, but shows the confined volume, referred to as the transfer machine, removed from the other confined volume, both confined volumes being isolated from the external environment.

In the confined volume 3 referred to as the transfer machine, materials will be held such as that shown by the sketch M for transfer into the container 1 forming the isolating chamber or vice versa, and there will also be contained in said transfer machine 3 at least one further closure piece 7X intended to be used for closing the confined volume 1, after completion of communication between the two confined volumes 1 and 3 and completion of the transfer of materials from one to the other of these volumes. This auxiliary closure piece 7X which may be contained in the confined volume 3 (but which could also be received in the stationary confined volume 1 where it would wait with other closure pieces) is also advantageously fitted with a cap 28 (see FIGS. 6 and 7), the perimeter of which is caused to adhere to the face of the membrane 14X of said auxiliary closure piece 7X which is opposite to the face joined to the bushings 10X and 12X. This cap 28 is shaped in such a way that it can also join up with the terminal edge of the part 9A of the rigid annular structure of said closure piece 7. Any gap Vx defined between the cap 28 and the membrane 14X of the auxiliary piece 7X to which the cap 28 is joined, is completely isolated from the external environment and hence cannot be contaminated by the environment of the confined volumes such as 1 and 3, in any of the operations to be described for the use of said auxiliary closure piece 7X.

Figure 4:
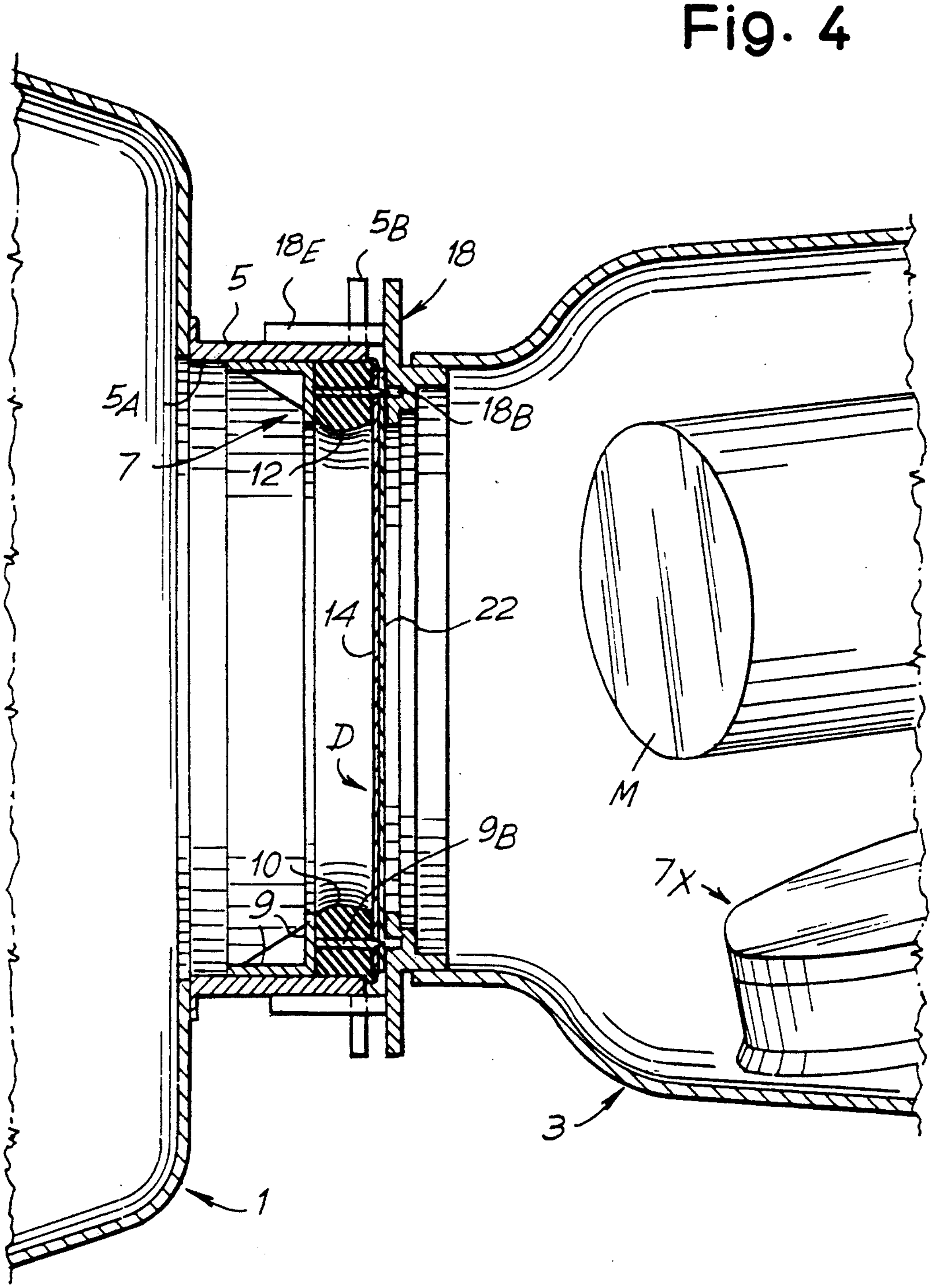
FIG. 4 is similar to FIG. 2 but shows the two confined volumes joined.
Figure 5:
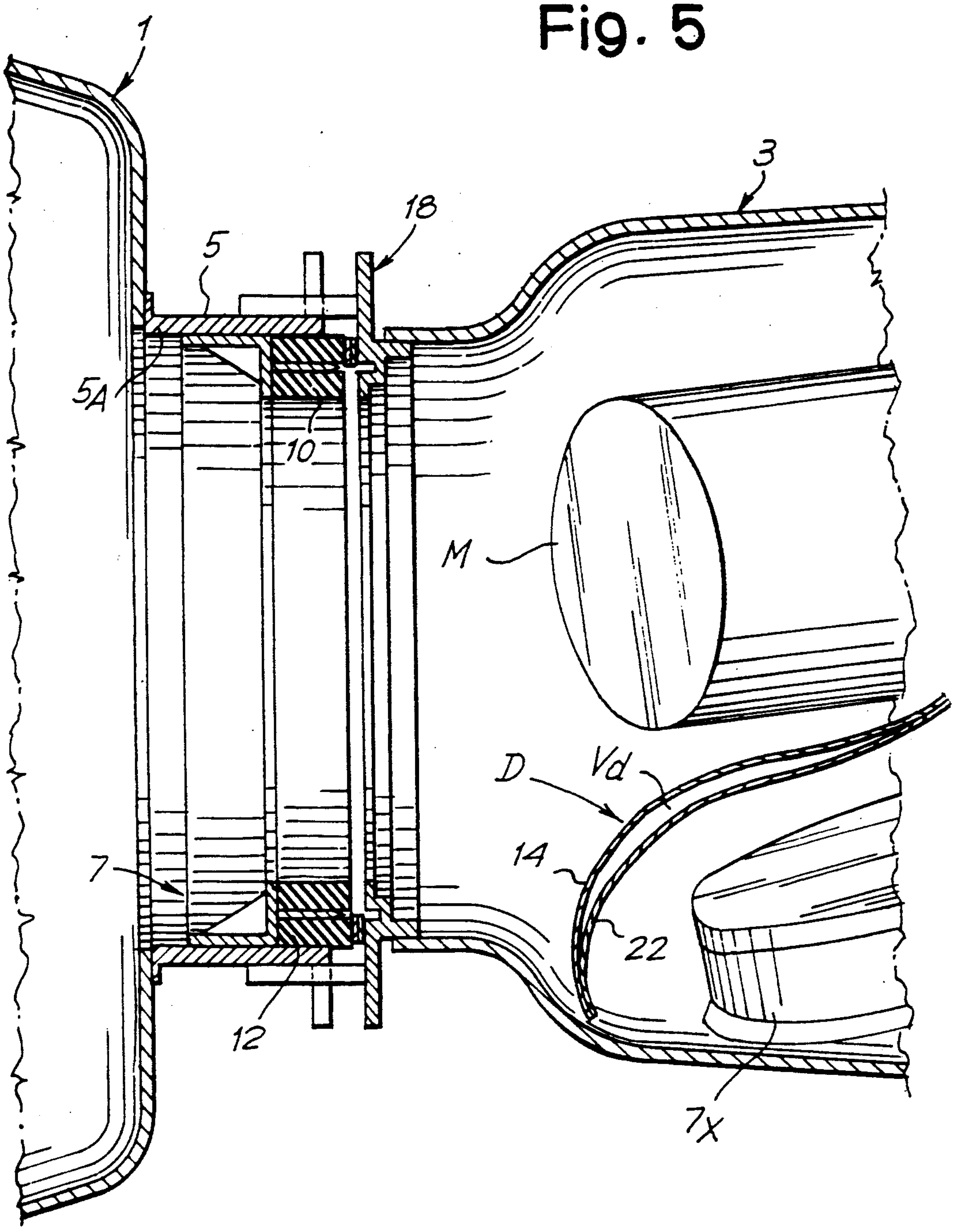
FIG. 5 shows the two confined volumes joined up and in communication with each other.

In the conditions shows in FIG. 2, the closure piece 7, received inside the connector 5 and with its own uncut membrane 14, isolates said confined volume 1 from the external environment, the membrane 14 projecting slightly beyond the outward extremity of the connector 5, that is beyond the flange structure 5B. The confined volume 3 (which may be a transfer machine) is brought forward in the direction of the arrow f3, guided in some suitable mechanical manner between the parts 18E and 5 until the two membranes 14 and 22 are joined up with each other; the two membranes are caused to adhere on their perimeter along their respective peripheral annular rings which correspond to the position of the bushings 10 and 12, and at least one of these bushings is fitted with an adhesive indicated by 30 for the membrane 14 and by 32 for the membrane 22 (see FIG. 3); before the joining operation, this adhesive 30 or 32 or each of these adhesives 30 and 32 will be protected by a suitable cover, such as a film or the like which is uncovered in order to activate the adhesive zone for the joining operation. When the confined volume 3 is brought against the connector 5 and the two membranes 22 and 14 join up, these membranes become sealed together around the two peripheral joining rings carrying the adhesive 30 and/or 32 and hence around two annular zones which correspond respectively to the bushing 10 and to the bushing 12. Completion of the approach causes joining by means of adhesion along the two peripheral rings of the membranes 14 and 22 under the action of the elastic pressure of the two bushings 10 and 12 which, as joining is completed as shown in FIG. 4, are compressed and hence react with pressure between the annular structure 9 and the wall 18A of the frame 18. The axial compression of the two bushings 10 and 12 results not only in the peripheral joining of the two membranes 14 and 22 but also in the activation of the annular cutting means 9B which now projects out of the compressed bushings and acts on the joined membranes, cutting them and entering the annular groove 18B lined up with said annular cutting means 9B. Thus, as a result of being cut, the two joined membranes 14 and 22 give rise to the formation of a discoid D (see FIGS. 4 and 5) formed from the portions of the two membranes 14 and 22 lying within the annular cutting means 9B and sealed together by the action of at least the adhesive 30 and/or 32 in the annular zone corresponding to the bushing 10; the two membranes thus form in the discoid D a new confined volume Vd which encloses the two originally external faces of the membranes 14 and 22. The remaining portion around the perimeter corresponding to the bushing 12 remains bonded owing to at least the cement 16 and cement 24 to the bushing 12 and to the frame 18. With the discoid D cut out in the manner described above, and the temporary mechanical join established between the two confined volumes 1 and 3 by mechanical connecting means cooperating between the flange 5B and the frame 18, the transfers of materials such as M are carried out between the two confined volumes in total isolation from the external environment. Along with the various materials, an auxiliary closure piece 7X is transferred from the confined volume 3 to the confined volume 1 (unless such an auxiliary closure piece 7X is already present in the confined volume 1); the transfer of an auxiliary closure piece such as 7X through the opening defined by the structure 9 of the closure piece 7 received inside the connector 3 and through the opening of the frame 18, occurs by virtue of the different dimensions of said opening in two mutually perpendicular axes. After the transfer between the two confined volumes has been completed, the auxiliary closure piece 7X is "stood in line" after the closure piece 7 inside the wall 5A, that is behind said piece 7 which leaves uncovered part of the wall 5A lying toward the interior of the container 1. Thus the perimeter of the cap 28 joins the wall 9A of the closure piece 7 whose membrane has been removed. The result is the conditions shown in FIG. 6. In this way the periphery of the cap 28 adheres to the membrane 14X of the auxiliary closure piece 7X and is also joined to the part 9A of the annular structure 9 of the piece 7, the center of whose membrane has been removed. The perimeter portion of the two joined and bonded membranes, resulting from the cutting out of the discoid D, establishes a bond between the frame 18 and the bushing 12 of the closure piece 7. Thus, by unmaking the mechanical connection between the frame 18 and the means connected to the flange 5B of the connector 5 and removing the transfer machine 3 away from the connector 5, the result is the retraction of the piece 7 and also of the cap 28 from the connector 5 after the retraction of the auxiliary closure piece 7X as far as the position indicated in FIG. 7 and corresponding to the position previously assumed by the piece 7 as shown in FIG. 2. The result is the renewal of the closure of the connector 5 to isolate the confined volume 1 from the external environment, and the removal of the transfer machine 3 which is still closed off from the external environment owing to the presence of the cap 28 which remains stuck to the part 9A of the closure piece 7 removed from the confined volume 1 along with the transfer machine 3. The discoid D too is removed along with the transfer machine 3 inside which it lies. The operation of inserting the auxiliary closure piece 7X from the interior of the confined volume 1 into the connector 5 is performed by the operator who can work in conditions of isolation inside the confined volume 1 or the confined volume 3. In either case the replacement is performed by pushing the auxiliary closure piece from the volume 1 or pulling it by the traction of the cap 28 from the volume 3. The cap 28 may be detached from the piece 7X by a mechanical loosening or snatching release action, with simultaneous attachment of said cap to the departing piece 7.

It should be observed that the isolation of the volume Vx of the gap between the membrane 14X and the cap 28, and the isolation of the environment from the volume Vd defined inside the discoid D between the two peripherally joined membranes, prevents any possibility of reciprocated contamination between these spaces Vx and Vd and the confined volumes of 1 and 3.

In a possible alternative embodiment, a suitable means for heating along the cutting line of the membranes may be provided. This heating means may be represented by a resistor extending along the groove 18B or combined with the annular part 9B of the cutting means and in either case in an arrangement allowing a heating and welding by fusion or plastification between the two membranes around the peripheral annular cutting zone, in order to seal the periphery of the discoid in addition to the sealing effect brought about by the adhesive coats 30 and/or 32 in the zones corresponding to the bushinges 10. A similar sealing action may be provided on the internal periphery of the annular remnant of the two joined membranes between the wall 18A and the bushing 12. Briefly, in FIG. 3, 40 indicates a possible position for these heating means, which may be positioned also on the outside of the groove 18B, or be combined with the cutting element 9B.

It will be understood that the drawing shows only an embodiment given purely as a practical demonstration of the invention, it being possible for said invention to vary as regards shapes and arrangements without thereby departing from the scope of the concept underlying said invention.

I claim:

1. Equipment for forming connections between discontinuous confined volumes, comprising:

an isolating chamber;

an annular connector provided on said isolating chamber, said annular connector defining an isolating chamber access opening, said access opening having a first access opening dimension which is greater than a second access opening dimension, said second access opening dimension being perpendicular to said first access opening dimension, said annular connector including an internal wall defining a substantially constant isolating chamber access opening cross section;

a closure piece including an annular member, a closure piece membrane and an annular cutting means for cutting said closure piece membrane and for cutting another membrane joined thereto;

a transfer machine including a frame defining a passageway slot and a transfer machine membrane fastened to said frame;

adhesive means associated with each of said closure piece membrane and said transfer machine membrane for adhering said membranes to each other to form joined membranes upon said isolating chamber and said transfer machine being joined up, said annular cutting means cutting said joined membranes to form a joined membrane discoid formed by at least two peripherally joined thicknesses of said joined membranes, said joined membrane discoid being movable into one of said isolating chamber and said transfer machine;

and an additional closure piece positioned in one of said isolating chamber and said transfer machine and being positionable in said annular connector from an interior of said isolating chamber to replace said closure piece of said joined membranes.

2. Equipment according to claim 1, wherein said closure piece is formed including two comparatively soft concentric annular bushings including an outer bushing forming a seal with said internal wall of said annular connector, said adhesive means being provided as an adhesive peripheral frontal surface on said outer bushing, said annular cutting means being positioned between said concentric annular bushings and projecting from said annular bushings when compressed frontally from an outer side, said first membrane being fixedly connected to said adhesive peripheral frontal surface and having on an outer surface with an adhesive peripheral annular ring corresponding to a frontal surface of said two concentric annular bushings, said frame having an annular frontal surface corresponding to said annular bushings and having an intermediate annular groove cooperating with said annular cutting means and separating said annular frontal surface into two concentric annular zones, said transfer machine having an outer peripheral zone formed of adhesive corresponding to an outer annular bushing of said annular frontal surface, said transfer machine annular membrane being engaged to said outer peripheral zone, said adhesive means further including a peripheral annular ring formed of adhesive material provided on an outer surface of said transfer machine membrane, said additional closure piece being positioned in said transfer machine.

3. Equipment according to claim 1, wherein said additional closure piece is fitted with a cap, said additional closure piece including a membrane covered by said cap, said cap being on a surface facing away from said isolating chamber when said additional closure piece is installed, said cap being detachable from said subsequent closure piece and being joinable to said closure piece for removal of said closure piece with said transfer machine.

4. Equipment according to claim 1, further comprising heating means cooperating with said annular cutting means for form an annular remnant along a cutting line providing a seal between said isolating chamber membrane and said transfer machine membrane.

5. Equipment according to claim 1, wherein said annular connector cooperates with said frame to define flange connection means for forming an external mechanical connection between said connector of said isolating chamber and said frame of said transfer machine.

6. Equipment according to claim 1, wherein each of said isolating chamber annular membrane and said transfer machine annular membrane includes an adhesive annular ring and a removable cover covering said adhesive annular ring.

7. Equipment according to claim 1, wherein said discoid forms a further confined volume.

8. Equipment according to claim 2, wherein said closure piece and said cap forms further confined volume.

9. Equipment for forming connections between discontinuous confined volumes, comprising;

an isolating chamber with an annular connector defining an access opening with an internal wall of constant section, and with one dimension greater than another dimension perpendicular thereto;

a closure piece, said constant section of said internal wall allowing the sliding of said closure piece within said access opening, said closure piece including an annular structure, two comparatively soft concentric annular bushings, a first bushing of said annular bushings being designed to form a seal with said inner wall and having an adhesive peripheral frontal surface, an annular cutting means placed between said concentric annular bushings and designed to project from said concentric annular bushings when said bushings are compressed frontally from the outside and a first membrane for closing off the isolating chamber, peripherally anchored to said adhesive peripheral frontal surface, and having on an outer surface an adhesive peripheral annular ring corresponding to the frontal surfaces of said two concentric annular bushings;

a transfer machine including a frame defining a passageway slot and having an annular frontal surface corresponding to that of said annular bushings and having an intermediate annular groove designed to cooperate with said annular cutting means and separating two concentric annular zones in said annular frontal surface, a transfer machine membrane for closing the transfer machine, said transfer machine membrane being engaged on an outer peripheral zone which is made of adhesive provided on said annular frontal surface, an adhesive peripheral annular ring on an outer surface of said transfer machine membrane;

an additional closure piece, positioned in said transfer machine, for the closing of said access opening in the annular connector, whereby said isolating chamber and said transfer machine may be joined at said first membrane and said transfer machine membrane which adhere to each other by means of their respective adhesive peripheral annular rings to form joined membranes and said joined membranes are cut by said annular cutting means to define with said membranes a discoid with at least two peripherally joined thicknesses, which can be removed into one of said isolating chamber and said transfer machine to provide the passage between the two said confined volumes.

* * * * *